United States Patent

Harris et al.

[11] 4,046,814
[45] Sept. 6, 1977

[54] PREPARATION OF DIKETONES

[75] Inventors: Frank W. Harris, Xenia; Bruce A. Reinhardt, Dayton, both of Ohio

[73] Assignee: Wright State University, Dayton, Ohio

[21] Appl. No.: 641,959

[22] Filed: Dec. 18, 1975

[51] Int. Cl.$^2$ .................. C07C 49/76; C07C 45/00; C07D 307/12; C07C 121/60; C07D 307/46; C07D 213/50

[52] U.S. Cl. .................. 260/590 E; 260/590 D; 260/297 R; 260/347.8; 260/50; 260/465 H; 260/515 P; 260/558 R; 560/54

[58] Field of Search ......... 260/590 R, 590 D, 465 D, 260/465 H, 515 R, 515 P, 182, 297 R, 592, 347.8, 182

[56] References Cited

U.S. PATENT DOCUMENTS

| 3,661,850 | 5/1972 | Stille | 260/50 |
|---|---|---|---|
| 3,749,740 | 7/1973 | Sutton | 260/465 H |
| 3,780,005 | 12/1973 | Sutton | 260/465 H |
| 3,780,064 | 12/1973 | Weinstock | 260/465 H |
| 3,829,497 | 8/1974 | Wentworth | 260/590 D |
| 3,852,243 | 12/1974 | Hergenrother | 260/50 |

OTHER PUBLICATIONS

Hickenbottom, "Reactions of Organic Compounds," pp. 381-383 (1957).
Morrison et al., "Organic Chemistry," 2nd Ed., pp. 939-940 (1966).
House, "Modern Synthetic Reaction," pp. 510-515 (1972).

*Primary Examiner*—James O. Thomas, Jr.
*Assistant Examiner*—James H. Reamer
*Attorney, Agent, or Firm*—Biebel, French & Nauman

[57] ABSTRACT

A method for preparing diketone starting materials useful in synthesizing tetraketone precursors for high temperature resistant polyquinoxaline resins. Dicarboxylic acid derivatives that contain no alpha hydrogens are contacted in the presence of a strong base with an active-hydrogen compound of the type $R - CH_2 - X$ where R is an aryl, substituted aryl, heterocyclic or substituted heterocyclic radical and X is a nitrile group or a carboxylic acid functional group. A reaction intermediate is formed having the formula:

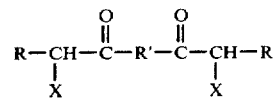

wherein R and X are as defined in regard to the active-hydrogen compound and R' is the same as R. The reaction intermediate is hydrolyzed and decarboxylated to form the diketone. The diketones produced by the instant invention have the formula:

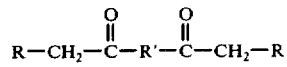

where R and R' are the same as in the reaction intermediate.

8 Claims, No Drawings

PREPARATION OF DIKETONES

CROSS-REFERENCE TO RELATED APPLICATIONS

Reference is made to applicants' copending application Ser. No. 641,958, filed on even date herewith and assigned to the same assignee.

BACKGROUND OF THE INVENTION

The present invention relates to a method for producing diketones of a type which are themselves useful in the production of certain tetraketones which may be used for the manufacture of thermally stable quinoxaline polymers.

Polyquinoxaline resins have become widely sought after in recent years due to their unique thermal properties. Because of their desirable properties, the polymers are useful for high temperatures adhesives, coatings and films in a number of critical industries. As stated in Stille, U.S. Pat. No., 3,661,850, polyquinoxaline polymers are "suitable for high temperature electrical insulators, battery separators,foams, ablative materials for re-entry bodies and rocket nozzles." Other patents which discuss these unique resins, their properties and uses are: Augl, U.S. Pat. Nos. 3,766,141 and 3,642,700; and Hergenrother, U.S. Pat. No. 3,778,412.

Stille, Augl and Hergenrother all disclose methods of preparing polyquinoxalines from tetraketones of the following general formula:

$$R-\overset{O}{\underset{\|}{C}}-\overset{O}{\underset{\|}{C}}-R'-\overset{O}{\underset{\|}{C}}-\overset{O}{\underset{\|}{C}}-R$$

In Stille R is said to be selected from the group consisting of alkyl, aryl, alkaryl, and aralkyl groups and hydrogen, while R' is selected from the group consisting of alkylene, arylene, aralkylene and alkarylene groups (Col. 3, lines 6–16). Similarly in Augl, R is listed as $C_6H_5$ or H and R' is m-phenylene, p-phenylene or a number of diphenyl compounds (Col. 2, lines 29–64 of the U.S. Pat. No. 3,766,141). In Hergenrother, R is stated to be hydrogen, alkyl, phenyl and substituted phenyl and R' is for the most part selected from a number of divalent alkyl, phenyl and diphenyl compounds (Col. 3, lines 1–34).

These prior art patents list several methods of preparing the desired tetraketone precursors used in manufacture of the polyquinoxaline resins. Included are methods which utilize a diketone having the formula $$R-CH_2-\overset{O}{\underset{\|}{C}}-R'-\overset{O}{\underset{\|}{C}}-CH_2-R$$

or $$R-\overset{O}{\underset{\|}{C}}-CH_2-R'-CH_2-\overset{O}{\underset{\|}{C}}-R$$

wherein R and R' are as defined above by the patentees in regard to the tetraketones. Thus, Hergenrother and Augl both disclose methods wherein diketones are oxidized to tetraketones with selenium dioxide or selenious acid. (Hergenrother, Examples 3-5; Augl, Col. 3, lines 3–36).

The diketones themselves are said to be produced by any number of methods. For example, Augl in U.S. Pat. No. 3,766,141 discloses a reaction in which certain diketones are prepared by reacting dicarboxylic acid derivatives under standard conditions with thionyl chloride to form the acid chloride compound. The acid chloride compound is then reacted with benzene and aluminum chloride under typical Friedel-Crafts conditions to obtain a phenylacetyl compound (Col. 3, lines 3–36).

See also, Hergenrother (U.S. Pat. No. 3,778,412) which suggests preparation of p,p'-diacetyldiphenyl ether by Friedel-Crafts acetylation of diphenyl ether in methylene chloride (Example 3); preparation of p,p'-di(-phenylacetylphenyl) ether by mixing diphenyl ether and phenylacetyl chloride in methylene chloride, adding that mixture to a suspension of anhydrous aluminum chloride in methylene chloride under nitrogen, and separating and recrystallizing (Example 4); and preparing p-di (phenacyl) benzene from a benzene solution of the diacid chloride of p-phenylenediacetic acid which was added to a slurry of anhydrous aluminum chloride (Example 5).

The use of Friedel-Crafts reactions for production diketones is, of course, commercially feasible. In fact, the disclosed systems are quite popular. However, in a number of instances the costs are excessive because of the expense in obtaining the starting materials. Likewise, these reactions do not offer a large degree of flexibility in the steps involved or the production of some of the moe exotic diketones.

It is also known that certain other diketones of this type may be obtained via the reactions of the appropriate dinitriles with Grignard reagents. However, this process is expensive due to the fact that, although the reactions are run in very dilute solutions, a large percentage of the Grignard reagent is lost through coupling. In fact, only a few diketones of this type have been synthesized because several functional groups, such as amino groups, hydroxyl groups, nitro groups, etc., react with Grignard reagents and, therefore, cannot be present in the starting materials.

Accordingly, the practical usefulness of the prior art process has been considerably limited. Therefore, the need exists for an improved process for producing large quantities of diketones as inexpensively as possible.

SUMMARY OF THE INVENTION

In accordance with the present invention, there is provided a method for economically producing large amounts of diketones of the type;

$$R-CH_2-\overset{O}{\underset{\|}{C}}-R'-\overset{O}{\underset{\|}{C}}-CH_2-R \qquad (I)$$

where R and R' are aryl radicals, substituted aryl radicals, heterocyclic radicals, or substituted heterocyclic radicals.

The instant method for preparing diketones of this type involves the reaction of dicarboxylic acid derivatives that contain no alpha hydrogens (i.e., aromatic diesters, substituted aromatic diesters, heterocyclic diesters, aromatic diacylhalides, etc.) with active-hydrogen compounds of the type:

(II) $R - CH_2 - X$ where R is as defined with reference to Formulas I and X is a nitrile group or a carboxylic acid functional group, such as a carboxylic ester, a carboxylic amide, etc. The reaction is carried out in the presence of a strong base such as sodium hydride, sodium amide, sodium triphenylmethyl, etc.

A reaction intermediate is formed having the formula

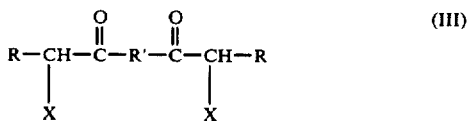

wherein R and R' are as defined in reference to Formula I and X is a nitrile or a carboxylic acid functional group. This reaction intermediate is, then, hydrolyzed and decarboxylated to form the diketone.

Diketones of Formula I prepared in this manner may be oxidized to the corresponding tetraketone by the methods of Augl, Hergenrother, or as disclosed in copending application Ser. No. 641,958. The tetraketones can then be used to prepare the desired polyquinoxaline resins by any of the enumerated prior art methods.

Accordingly, it is an object of the present invention to provide an inexpensive means to produce large quantities of diketones which may be used as the starting material in preparation of tetraketone precursors for use in manufacturing thermally stable polyquinoxaline resins.

Other objects and advantages of the invention will be apparent from the following description and the accompanying claims.

DESCRIPTION OF THE PREFERRED EMBODIMENTS

The reaction of the present invention to produce diketones of formula I can be carried out with or without a solvent, but for ease of operation, i.e., separation of unreacted base from the product, etc., it is generally carried out in an inert solvent. The active-hydrogen compound of formula II and the base are mixed in an inert, anhydrous, liquid solvent at a temperature of from about −100° C. to about 200° C., and then the dicarboxylic acid derivative is added. The reaction time can vary considerably, as, for example, from 10 minutes to 10 hours. The relative amount of the base employed to the active-hydrogen compound used can vary from an equal molar amount to a very large excess, but generally a three molar excess of base is used. Any anhydrous liquid solvent that is inert under the reaction conditions can be used. Examples are: liquid ammonia; aliphatic, cycloaliphatic, or aromatic hydrocarbons; chlorinated hydrocarbons; ethers; etc. The selection of the solvent and the temperature used will depend upon the base being used, the active-hydrogen compound used, etc.

A reaction intermediate of formula III is formed. It can be isolated by evaporating the solvent if one has been used, and converted to the corresponding diketone by heating with water or an acid, such as sulfuric acid, hydrochloric acid, phosphoric acid, acetic acid, etc., or mixtures of these acids. The conversion, which involves hydrolysis and decarboxylation, is carried out at a temperature of from about 50° to about 250° C for a time sufficient to effect substantial reaction. The reaction time can vary from 1 hour to 48 hours. Alternately, the intermediate can be converted without isolation to the corresponding diketone in situ by adding the acid or mixture of acids to the reaction mixture and heating at a temperature of from about 50° to about 200° C. for a period of from about 1 hour to about 48 hours.

The reaction intermediate of formula III can also be converted to a di(beta-ketocarboxylate) salt in situ or after isolation by reaction with a base, such as sodium hydroxide, barium hydroxide, etc., or mixture of these hydroxides, under mild conditions. The hydrolysis is run in dilute base at a temperature of from about 0° to about 50° C. for a period of from about one hour to forty-eight hours. The salt is then decarboxylated by heating with water or an acid, such as, sulfuric acid, hydrochloric acid, etc., at a temperature of from about 25° to about 200° C. for a period of from about 1 hour to 48 hours.

Less preferably, the conversion of certain of the reaction intermediate of Formula III to the corresponding diketone can also be carried out by multi-step procedures. In a three-step procedure, where a nitrile group is used as the active-hydrogen compound, the di(beta-ketonitrile) intermediate can be converted to the corresponding di(beta-ketoamide) by treatment with various acidic or basic reagents, such as concentrated sulfuric acid at room temperature, acetic acid and boron fluoride, hydrogen peroxide and sodium hydroxide, hydrochloric acid followed by water, etc. This conversion can also be carried out by treatment with non-acidic or non-basic reagents, as, for example, water and nickel, manganese dioxide in methylene chloride, etc. The di(beta-ketoamide) is then further hydrolyzed to the corresponding di(beta-ketoacid) with either acidic or basic catalysts. In difficult cases, nitrous acid may be used. The di(beta-ketoacid) is converted to the diketone by simply heating or by heating with water, acidic reagents, or basic reagents.

In a two-step procedure where a nitrile group is used as the active-hydrogen compound, the di(beta-ketonitrile) intermediate is first converted to the corresponding di(beta-ketoester), which would itself be the intermediate if an ester group is used as the active hydrogen compound, by treatment with an alcohol and an acid or base. The di(beta-ketoester) is then decarboxylated by heating with water or acids. Non-acidic reagents, such as lithium iodide, may also be used to catalyze the decarboxylation. Several permutations and combinations of the described three-step and two-step procedures may also be used to affect the desired conversion of the reaction intermediate to the diketone, as, for example, a di(beta-ketoester) intermediate can be hydrolyzed to the corresponding di(beta-ketoacid) and then decarboxylated, etc.

Any aromatic or heterocyclic dicarboxylic acid derivative that contains no alpha hydrogens can be converted to the corresponding diketone by the process of this invention. Exemplary are the following known and commercially available compounds: dimethyl terephthalate, terephthaloyl dichloride, dimethyl isophthalate and isophthaloyl dichloride.

Any nitrile or carboxylic acid derivative that contains two alpha hydrogens can be used as the active-hydrogen compound of Formula II in the process of this invention. Exemplary are the following known and commercially available compounds: ethyl phenylacetate, ethyl 2-pyridylacetate, phenylacetamide, phenylacetonitrile, 4-aminophenylacetonitrile, methyl 4-biphenylacetate, 4-methylphenylacetonitrile, 3-chlorophenylacetonitrile, 5-fluoro-2-nitrophenylacetonitrile, 2-furanacetonitrile and 2-benzimidazolylacetonitrile.

The reaction intermediate of general Formula III formed by use of dicarboxylic acid derivatives and active hydrogen compounds of Formula II include:

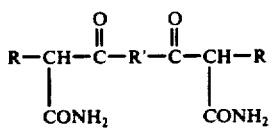

where R and R' are as defined with reference to Formulas I-III;

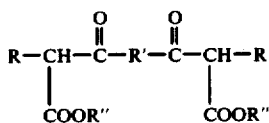

where R and R' are as defined previously and R" is hydrogen or an alkyl radical containing 1 to 10 carbon atoms, or an aryl radical or substituted aryl radical containing at least 6 carbon atoms;

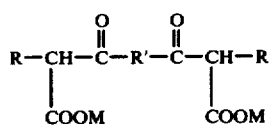

where R and R' are as defined previously and M is a metal ion; and

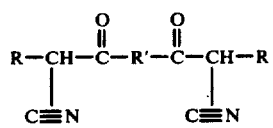

where R and R' are as defined previously.

The following examples will illustrate the process of preparing diketones in accordance with this invention.

EXAMPLE I

This example illustrates the preparation of 1,4-bis (phenylacetyl)benzene from dimethyl terephthalate and phenylacetonitrile. To a stirred suspension of 0.9 mole sodium hydride in 200 ml. of monoglyme was added 0.3 mole phenylacetonitrile. After the mixture was stirred for 40 minutes at room temperature, 0.15 mole dimethylterephthalate was added. The reaction mixture was then heated at 80° C for 2 hours. During this time the evolution of hydrogen, which started immediately upon the addition of the diester to the reaction mixture, gradually ceased. The monoglyme was removed under reduced pressure and the residue added to one liter of ice water. After the unreacted starting material was extracted with three 250 ml. portions of ether, the di(betaketonitrile) intermediate was precipitated in 80 ml. of concentrated hydrochloric acid. The solid was collected by filtration, washed with 300 ml. of 10% sodium bicarbonate, washed with 300 ml. of water, and dried at 100° C. for 4 hours.

To a solution of 0.10 mole of the di(beta-ketonitrile) in 1 liter of glacial acetic acid heated at reflux was slowly added 200 ml. of a 50% sulfuric acid solution. The reaction mixture was heated at reflux for 24 hours, cooled, and filtered to yield 0.08 mole of crude product. The product was recrystallized from ethyl acetate to afford 0.07 mole of pure 1,4-bis(phenylacetyl)benzene.

EXAMPLE 2

This example illustrates the preparation of 1,3-di (2-pyridylacetyl)benzene from terephthaloyl dichloride and ethyl 2-pyridylacetate. To a stirred suspension of 0.9 mole sodium hydride in 200 ml. of diglyme was added 0.3 mole of ethyl 2-pyridylacetate. After the mixture was stirred for 1 hour at room temperature, it was cooled to 0° C and 0.15 mole of terephthaloyl dichloride was added. After the exothermic reaction subsided, the reaction mixture was heated at 80° C for 2 hours. The diglyme was removed under reduced pressure and the residue added to one liter of ice water. After the unreacted starting material was extracted with three 250 ml. portions of ether, the di(beta-ketoester) intermediate was precipitated in 80 ml. of concentrated hydrochloric acid. The solid was collected by filtration, washed with 300 ml. of 10% sodium bicarbonate, washed with 300 ml. of water, and dried at 100° C for 4 hours.

The di(beta-ketoester) and 100 ml. of water were placed in a 1 liter steel pressure vessel. The vessel was sealed, heated as rapidly as possible to 185-195°, and kept at this temperature for 10-15 minutes. The reaction vessel was cooled to room temperature and the gas pressure carefully released. The water was removed under reduced pressure and the liquid residue solidified by stirring in hexane to afford crude 1,3-bis(2-pyridylacetyl)benzene.

While the methods herein described constitute preferred embodiments of the invention, it is to be understood that the invention is not limited to these precise methods, and that changes may be made therein without dparting from the scope of the invention which is defined in the appended claims.

What is claimed is:

1. The method of preparing a diketone having the formula

wherein R' is phenyl and R is a radical selected from the group consisting of phenyl, substituted phenyl, pyridyl, and furyl radicals, comprising: (a) reacting a dicarboxylic acid derivative that contains no alpha hydrogens selected from the group consisting of dimethyl terephthalate; terephthaloyl dichloride, dimethyl isophthalate and isophthaloyl dichloride with an active-hydrogen compound selected from the group consisting of ethyl phenylacetate, phenylacetamide, phenylacetonitrile, ethyl 2-pyridylacetate, 4-aminophenylacetonitrile, methyl 4-bi-phenylacetate, 4-methylphenylacetonitrile, 3-chlorophenylacetonitrile, 5-fluoro-2-nitrophenylacetonitrile, 2-furanacetonitrile and 2-benzimidazolylacetonitrile, said reaction taking place at −100° C to 200° C for 10 minutes to 10 hours and in the presence of a strong base selected from the group consisting of sodium hydride, sodium amide, and sodium triphenylmethyl to form an intermediate having the formula

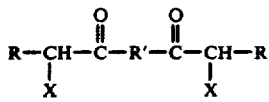

wherein R and R' are as defined and X is a nitrile or a carboxylic acid functional group, and (b) hydrolyzing and decarboxylating said intermediate to form said diketone.

2. The method of claim 1 wherein said hydrolyzing and decarboxylating of said intermediate is accomplished by treating said intermediate with water or acid at from about 50° to 250° C for between 1 nd 48 hours to form said diketone.

3. The method of claim 1 wherein said dicarboxylic acid derivative is added to a mixture of said active-hydrogen compound and said strong base in an inert solvent.

4. The method of claim 3 wherein said intermediate is isolated prior to hydrolyzing and decarboxylating.

5. The method of claim 4 wherein said isolated intermediate is treated with a base at from about 0° C to about 50° for from 1 hour to 48 hours followed by heating with water or an acid at from about 25° C to 200° C for from 1 to 48 hours to form said diketone.

6. The method of claim 1 wherein said strong base is sodium hydride.

7. The method of claim 1 wherein said dicarboxylic acid is dimethyl terephthalate.

8. The method of claim 7 wherein said active-hydrogen compound is phenylacetonitrile and said diketone produced is 1,4-bis(phenylacetyl) benzene.

* * * * *